US005554025A

United States Patent [19]
Kinsel

[11] Patent Number: 5,554,025
[45] Date of Patent: Sep. 10, 1996

[54] DISPOSABLE POINT OF USE AIR AND WATER FILTER FOR DENTAL SYRINGES

[75] Inventor: David I. Kinsel, Sylvania, Ohio

[73] Assignee: Gelman Sciences, Ann Arbor, Mich.

[21] Appl. No.: 397,397

[22] Filed: Mar. 2, 1995

[51] Int. Cl.⁶ ............................................. A61C 17/02
[52] U.S. Cl. ................. 433/80; 210/321.64; 210/321.75
[58] Field of Search .................. 433/80, 81, 84, 433/85, 88; 210/321.64, 321.72, 321.75, 321.84

[56] References Cited

U.S. PATENT DOCUMENTS

| | | |
|---|---|---|
| 4,950,159 | 8/1990 | Hansen ........................................ 433/80 |
| 5,204,004 | 4/1993 | Johnston et al. ........................ 210/651 |
| 5,370,534 | 12/1994 | Wolf et al. ................................. 433/80 |
| 5,474,451 | 12/1995 | Dalrymple et al. ....................... 433/80 |

OTHER PUBLICATIONS

"A Method of Decontamination of Ultrasonic Scalers and High Speed Handpieces", M. B. Dayoub, et al, *J. Periodontol.*, May, 1978, pp. 261–265.

Primary Examiner—Cary E. O'Connor
Attorney, Agent, or Firm—Brooks & Kushman P.C.

[57] ABSTRACT

A combination air and water microfiltration device suitable for mounting on a dental syringe handset contains microporous membrane air and water filters which prevent particulate and bacterial contamination of the air and water streams applied to a dental patient's oral cavity during dental procedures. The small pore size of the microporous membrane allows filtration of infectious agents while maintaining adequate flow rates.

13 Claims, 5 Drawing Sheets

DISPOSABLE POINT OF USE AIR AND WATER FILTER FOR DENTAL SYRINGES

TECHNICAL FIELD

The present invention pertains to a dual filter suitable for attachment to disposable dental syringe tips, and to an integral disposable dental syringe containing both air and water filtration devices as well as the syringe tip. The devices contain both hydrophilic and hydrophobic microporous membranes and are suitable for removing particulates, particularly microorganisms, as small as 1 µm in size or less.

BACKGROUND ART

Modern dental practices, whether associated with restoration or prophylaxis, involve both the influx of water and air into the patient's oral cavity as well as the ejection or removal of saliva and debris. While in prior years little attention was devoted to ensuring biologically pure water and air supplies, the reverse is now true, particularly in view of concerns with transmission of infectious diseases such as hepatitis and HIV, as well as concerns relative to previously unrecognized general systemic infection (sepsis) which may result when infectious agents encounter cut or abraded oral tissue.

Although heightened hygiene in dental work has fostered the wide-spread use of rubber gloves, face masks, and high temperature sterilization of dental implements, the air and water supplies, both of which are prime conduits for infectious agents, have received little attention. Compressed air supplies, for example, have been conditioned by traditional filter elements containing fibrous material, for example cotton or fiber glass. While such filters are effective to remove oil mist from compressors, dust, and other particulate matter of large dimension, they are of little effectiveness with regard to microbes such as bacteria, yeasts, fungi, and viruses. Moreover, the microbes which may be initially removed may reproduce in the filter elements themselves, ultimately contributing to microbe contaminated air.

Water supplies have also been traditionally filtered, either by fibrous or wound filters or by beds of activated carbon, zeolites, alumina, etc. Such beds and filters are notorious for harboring microbes, however, and thus such filters, while being effective to remove major particulates, and, in the case of activated carbon, organic contaminants, have only marginal effectiveness with respect to microorganisms, with even this marginal effectiveness being of short duration.

In U.S. Pat. No. 4,950,159 is disclosed a filter element for a dental syringe in which a longitudinal filter element divided into two compartments filters the water and air supplies just prior to dispersal from the syringe. However, the filtration elements are activated charcoal for the water supply and cotton fleece for the air supply. Neither of these filtration elements is well suited to eliminate microbes from the respective supplies. Moreover, the device allows contaminated air and water to be backflushed into the supply systems should a reduction in pressure occur, or even by remaining at static pressure for extended periods. In this manner, infectious agents may be transmitted from patient to patient. As the unit is of high cost, currently in the range of 20–30 dollars, it is not a one-time use disposable filter.

U.S. Pat. No. 5,204,004 discloses a filtration element for the water supply to a dental syringe, employing a microporous membrane. Unfortunately, the air supply is left unfiltered. The element is not readily adapted to the input fittings on many syringes in common use, and must instead be spliced into a split and cut water line. The '004 filtration is thus not a point of use device, nor it is subject to easy and rapid replacement. Finally, its location several inches upstream from the syringe leaves several inches of tubing which may contain a biologically active microbial coating along its interior surface.

SUMMARY OF THE INVENTION

The present invention overcomes the impediments of prior art devices by providing a compact, disposable, point of use filter element which filters both the air and water supply to a dental syringe, the filtration effective to retain microorganisms. The subject device attaches readily to standard syringes and additionally provides protection against contamination of the water and/or air supply lines from microbes which might be derived from the patient by eliminating the potential for backflushing. The above benefits, features, and advantages of the present invention are readily apparent from the following detailed description of the best mode for carrying out the invention when taken in connection with the accompanying drawings.

BRIEF DESCRIPTION OF THE DRAWINGS

FIG. 7b illustrates a cylindrical housing suitable for use with the embodiment of FIG. 7a; and FIG. 8 illustrates an end view of a planar filter element suitable for use with the embodiment of FIG. 7a.

DESCRIPTION OF THE PREFERRED EMBODIMENTS

The subject filter device is adapted in its various embodiments to be readily mountable onto a standard dental syringe, and may be adapted so as to receive an autoclavable or disposable syringe tip. In one embodiment, the syringe tip is an integral part of the device.

The air and water supplies of the A-dec syringe, an industry standard, are supplied concentrically, the water being supplied from an inner tube, while a clearance between the outside diameter of this inner tube and an outer tube supplies air. The syringe handset is equipped with a bore in its outlet face or fitting, the bore having an annular groove, displaced from the outlet face, containing a sealing and retaining elastomeric O-ring. In use, autoclavable or disposable tips having a diameter providing a sliding fit into the handset bore, and a mating annular groove to receive the sealing O-ring are inserted into the handset bore. Following use with a given patient, the durable syringe tips are sterilized by high pressure autoclaving, while the disposable tips are thrown away.

The filter device of the subject invention may be secured to the handset by an intermediate adapting member. Such adapting members may facilitate adaptation to non-standard handsets while retaining but a single filter design. In such cases, the adapter may itself be durable or disposable. Preferably, however, the subject filter device has a preferably axially located cylindrical extension containing a circumferential O-ring receiving groove substantially identical to the end of the standard syringe tips, in order that the subject filter devices may be readily mounted onto and detached from the handset.

The housing of the preferred filter device is a substantially planar device having a thickness suitable to retain the necessary filters, but otherwise as thin as possible. The cross-section in the plane of the device perpendicular to its axis is preferably circular, but square, rectangular, or other geometric shapes may be used as well without defeating the purpose of the device. Preferably, exterior corners are rounded to avoid sharp edges and potential snagging problems during dental work.

The filter device of the subject invention employs two microporous membranes, one for air filtration, and one for water filtration. The device retains distinctly separate air and water fluid pathways, with the filters positioned in such manner that all air and all water flowing through the device must pass through their respective filtration membranes. In the preferred embodiment the filters are positioned parallel to each other with the geometric center of each filter coincident with the axis of the device. In this preferred embodiment, the air filtration filter is in the shape of a doughnut or washer with a central opening, while the water filtration membrane is in the shape of a disk.

Figures 1A, 1B:
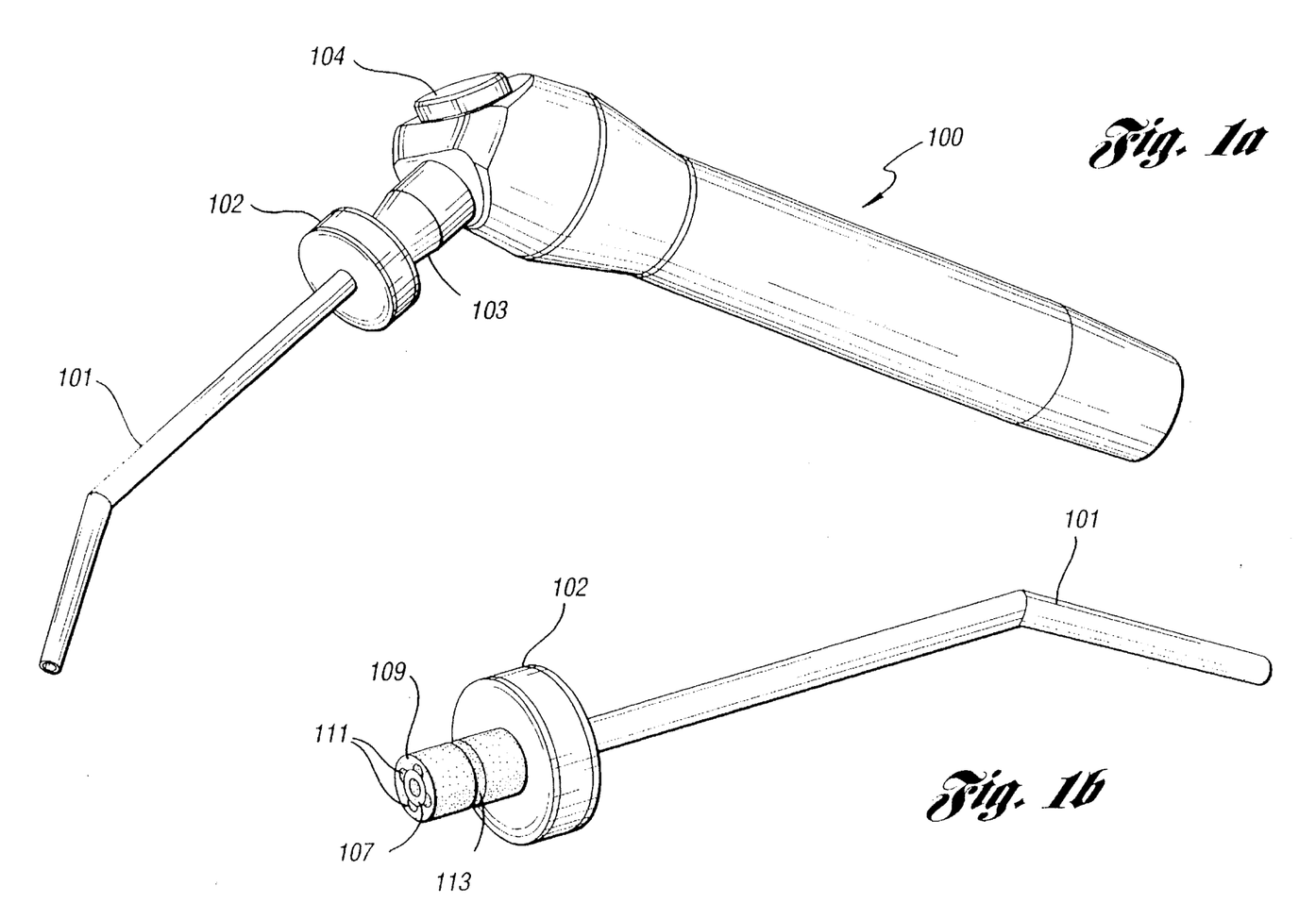
FIG. 1a illustrates a dental syringe with a disposable filter and integral syringe tip of the subject invention.
FIG. 1b illustrates the filter element and integral syringe tip showing the cylindrical connecting end with water and air inlets and O-ring groove.

The preferred embodiment is best understood with reference to the drawings. Many additional embodiments and adaptations will become evident to those skilled in the art of filter design. In FIG. 1a, a filter of the subject invention with integral tip is shown mounted to a standard dental handset 100. The syringe tip is shown at 101, the filter device at 102, the outlet nose or fitting of the handset at 103. At 104 is the button used to determine fluid flow: air, water, or a combination of water and air, from the device. In FIG. 1b is shown the filter/syringe tip assembly from the connecting end, showing the hollow, tubular water inlet tube 107, plastic sleeve 109 containing concentric air passages 111, and O-ring groove 113.

Figures 2, 3:
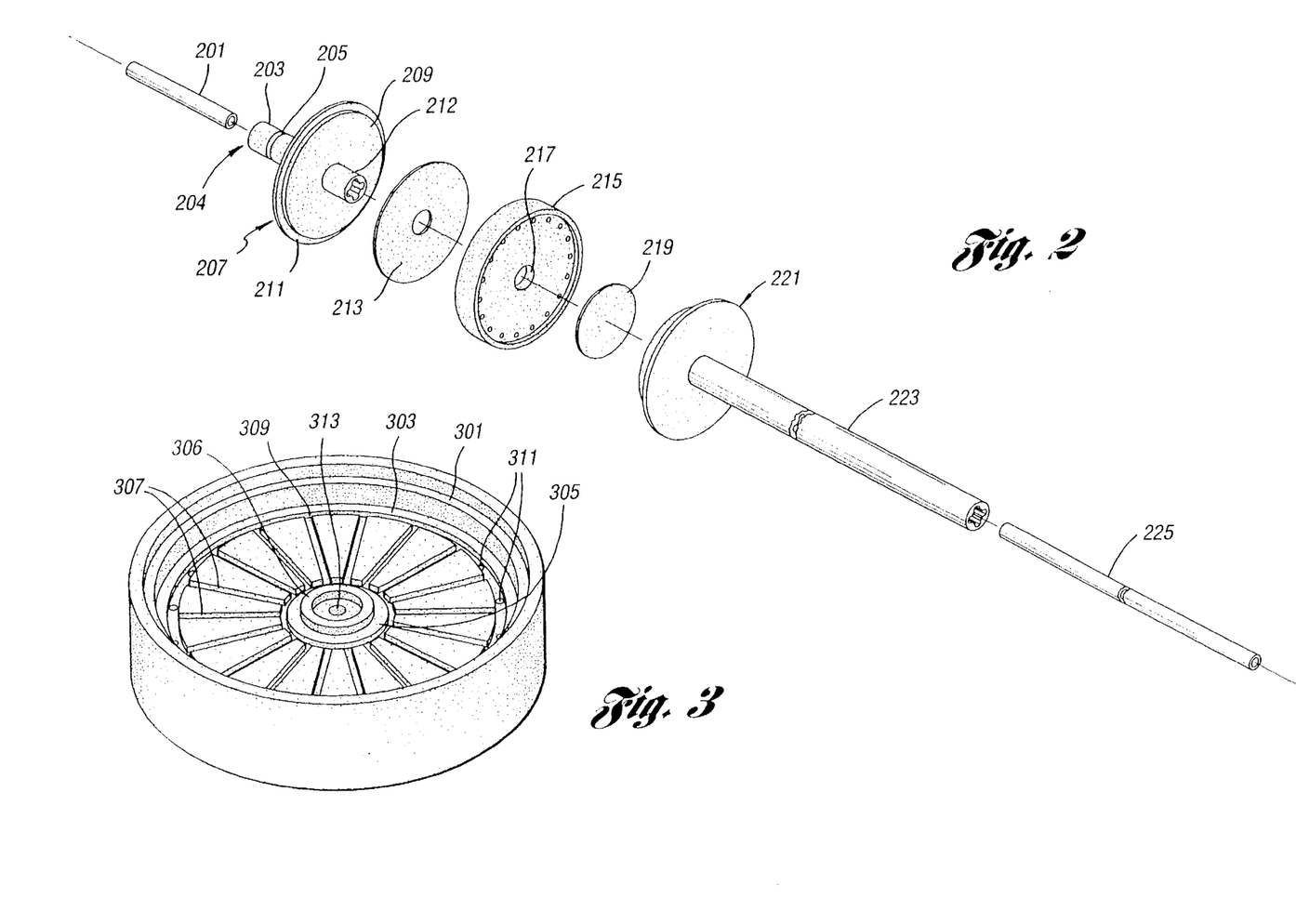
FIG. 2 illustrates an exploded view of one embodiment of the subject invention.
FIG. 3 illustrates the central grid of one embodiment of the subject invention from the side of the air filtration membrane.

Referring now to FIG. 2, an exploded view of the filter/syringe device illustrates the water inlet tube 201 and surrounding polymer sleeve connector 203 containing concentric air passages 204 and O-ring groove 205, as shown in FIG. 1b. Inlet housing 207 is preferably molded integral with connector 203, and has a portion of reduced diameter 209 on the outlet side, forming a shoulder 211 used to seal the device, preferably by solvent bonding, but optionally using other techniques such as ultrasonic welding. Connecting sleeve 203 extends inward of the inlet housing at 212, the sleeve at this point having radially extending passages through which air may flow from concentric passages 204 into the air filtration chamber which is formed upon assembly.

The washer-shaped air filtration microporous membrane is shown at 213. Upon assembly it is adhesive-bonded or thermal-bonded to raised annular steps on the inlet side of support grid 215. Grid 215 preferably has radially extending slots in the face abutting air filtration membrane 213 such that grid 215 provides both support for membrane 213 against the air pressure impinging upon it as well as providing for high flow passages for air. The radially extending slots terminate at a circumferential groove which is pierced with holes to allow filtered air to pass by grid 215. Grid 215 has a central opening 217 through which water inlet tube 201 passes.

At 219 is the water filtration microporous membrane, having a diameter less than that of the aforementioned circumferential groove, and sealed against a concentric raised portion of inlet housing 207. The water filtration membrane is supported against impinging water pressure by the inlet face of outlet housing 221, which, like disk 215, has radially extending slots on the inlet side facing water filtration membrane 219 to allow full fluid flow. Unlike disk 215, where air flow is toward the circumference of the device, water flow is toward the central axis. Syringe tip 223 is advantageously molded or inserted onto or into outlet housing 221 and is structured in the same manner as the connecting sleeve of inlet housing 207. Water outlet tube 225 is inserted into syringe tip 223, or the outlet housing and syringe tip may be molded around the water outlet tube. Following assembly, the combined air/water syringe may be bent to the angle desired for use.

FIG. 3 illustrates one embodiment of the central support grid 215 to which the air filtration microporous membrane is sealed. The device is disk-shaped with several radially concentric lands or shoulders. Shoulder 301 is a sealing shoulder against which the corresponding sealing surface of the inlet housing will be sealed, preferably by solvent bonding. Shoulder 303 is the surface onto which the outer periphery of microporous air filtration membrane will be bonded, for example by adhesive bonding, solvent bonding, thermal bonding, or ultrasonic welding. The inner periphery of the microporous membrane will be sealed to shoulder 305. When the device is assembled, the inner end of the inlet sleeve will approach the inner raised portion of the support disk at 306. Radially extending slots 307 allow for air flow from the sterile side of the filter to radially concentric groove 309 which contains through slots or holes 311 to allow air to flow through the disk. The disk further contains axial through passage 313 through which the water inlet tube passes, and to which the support grid is sealed.

Figure 4:
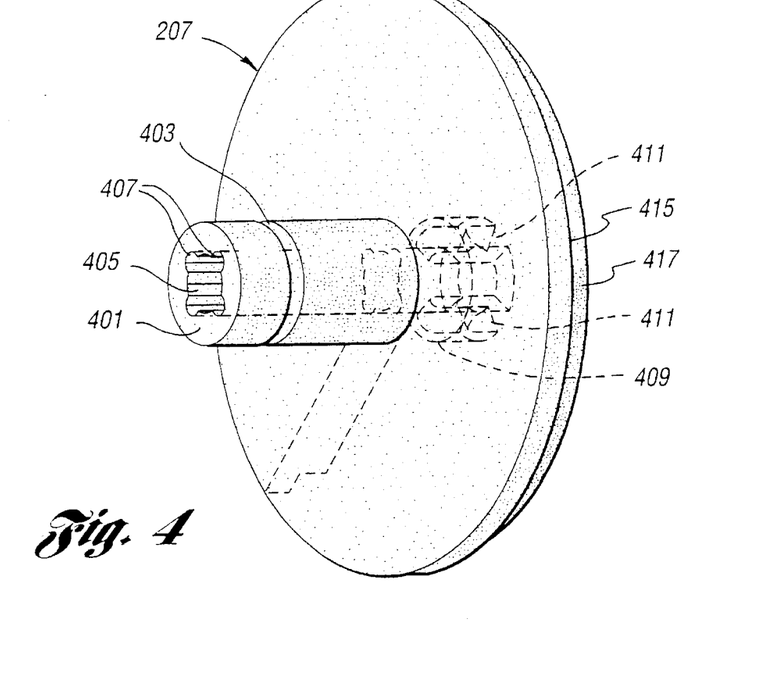
FIG. 4 illustrates in greater detail the inlet housing of one embodiment of the subject invention.

Referring to FIG. 4, the inlet housing 207 is shown without the water inlet tube, which may be inserted and bonded to the inlet sleeve or around which the inlet sleeve may be injection molded. The cylindrical connective sleeve 401 extends away from the face of the inlet housing and is dimensioned to slide into the mating bore in the syringe handset. At 403 is the annular groove adapted to receive the sealing O-ring located in the bore of the handset. Inlet bore 405 is dimensioned to receive the outer diameter of water inlet tube 201 (refer to FIG. 2), and additionally has recesses 407 to receive air flow. On the reverse side (outlet side) of inlet housing 207 is a corresponding extension 409 of the sleeve, with radially extending passages 411 connecting air recess passages 407 with the air chamber which is formed upon assembly.

On the outlet side of the device is a shoulder 415 formed by a reduced radiused section. The reduced radius section circumference 417 serves to position the inlet housing into the recess in the central grid upon assembly, the sealing face being the inlet side periphery of the disk shown at 301 in FIG. 3. Upon assembly, the innermost tip of water inlet tube 201 (FIG. 2) will pass through both the inlet housing 207 (FIG. 2) as well as through the grid 215 (FIG. 2) to supply water to the water filtration chamber.

Figure 5A:
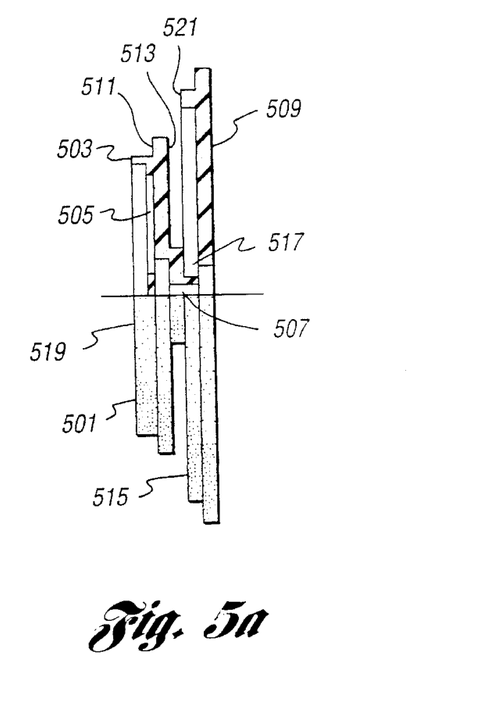
FIG. 5a illustrates in greater detail a cross-sectional view of an outlet housing of one embodiment of the subject invention.

Referring now to FIG. 5a is shown one embodiment of the outlet housing.

At 501 is the surface against which the water filter abuts, and is sealed around the periphery at 503. The surface 501 contains a membrane grid like that for the air filter, with radially extending slots 505 conducting water to the central opening 507 into which the outlet water tube (225 in FIG. 2) will be inserted from the outlet side 509 of the outlet housing. The outlet housing is sealed to the support grid (215 in FIG. 2) at shoulder 511. Outlet disk-like portion 513 is separated from outlet disk-like portion 515 by a separating space such that air may flow to central slotted openings 517 in a manner similar to that shown for the inward extension 409 with slots 411 in FIG. 4. The inlet side of outlet housing portion 519 is sealed to a sealing surface on the outlet side of the support disk (215 in FIG. 2), by shoulder 521. The sealing arrangements shown isolate the water path formed between inlet face 501 of the outlet housing and the support grid from the air path formed between portion 519 of the outlet housing and the support grid.

Figure 5B:
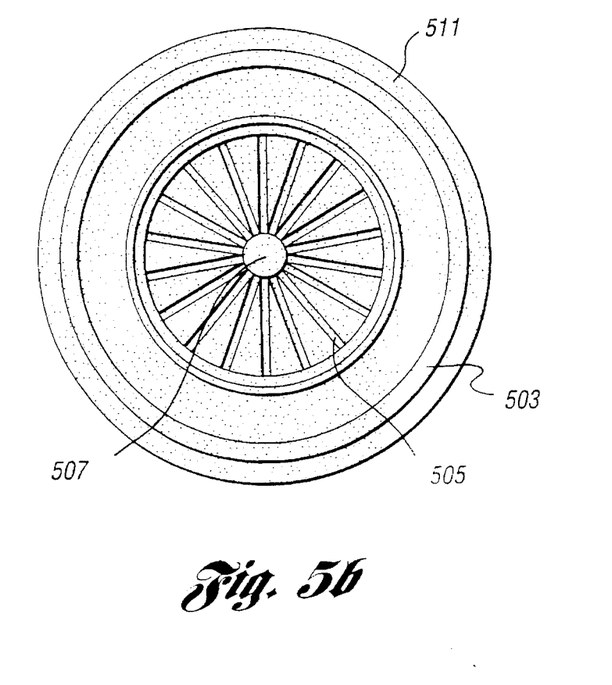
FIG. 5b illustrates a plan view of an outlet housing of FIG. 5a from the inlet side of the housing.

In FIG. 5b is shown the inlet face 501 of the support housing from the inlet side, showing the radial grid elements 505 (not all radial grooves are shown for clarity), the membrane sealing surface 503, the central water passage 507, and the surrounding water chamber sealing shoulder 511.

Figure 6:
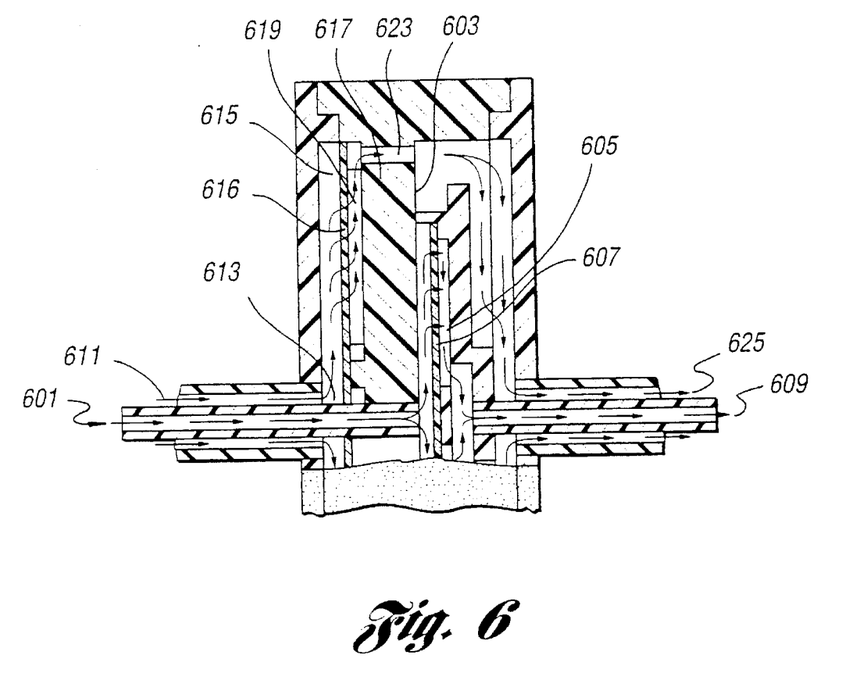
FIG. 6 illustrates a side view schematic of one embodiment of the subject invention showing the various fluid flow paths.

Referring now to FIG. 6 in simplified form, the flow paths may be shown. Water enters through the inlet tube at 601 and travels through the device until it reaches the outlet side of the support grid 603 where the water inlet tube terminates in water chamber 605. Water filter 607 filters the water, allowing it to pass into water outlet 609. Air enters the device at 611 and exits from the sleeve at 613, entering air chamber 615. After passing through air filtration membrane 616, the filtered air travels through radially extending slots 619 in support grid 617 and through holes or slots 623 in support grid 617 to the air outlet passage 625. As can be seen, separate flow paths for air and water are maintained.

Figure 7A:
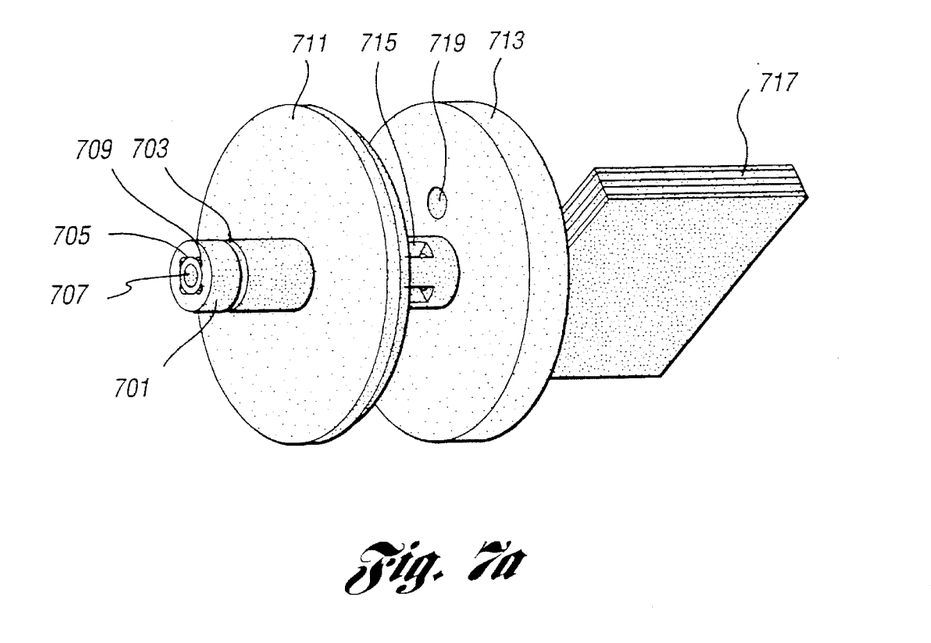
FIG. 7a illustrates an additional embodiment in which a dual purpose planar filter element is adapted to be inserted in a cylindrical housing.

Alternative embodiments are also contemplated. With reference to FIG. 7a, the inlet housing end and planar, dual function filtration grid, designed to be used in conjunction with a cylindrical housing, are shown. At 701 is the inlet sleeve with O-ring groove 703. The central, hollow, tubular water passage is at 705, with water entering at 707. Air enters the recesses 709 in the sleeve, as before. As in FIG. 4, the sleeve extends through outermost inlet housing portion 711, the water passage extending also through inlet housing portion 713. Air escapes into the space between portions 711 and 713 through slots 715, as shown also in FIG. 4.

Figure 7B:
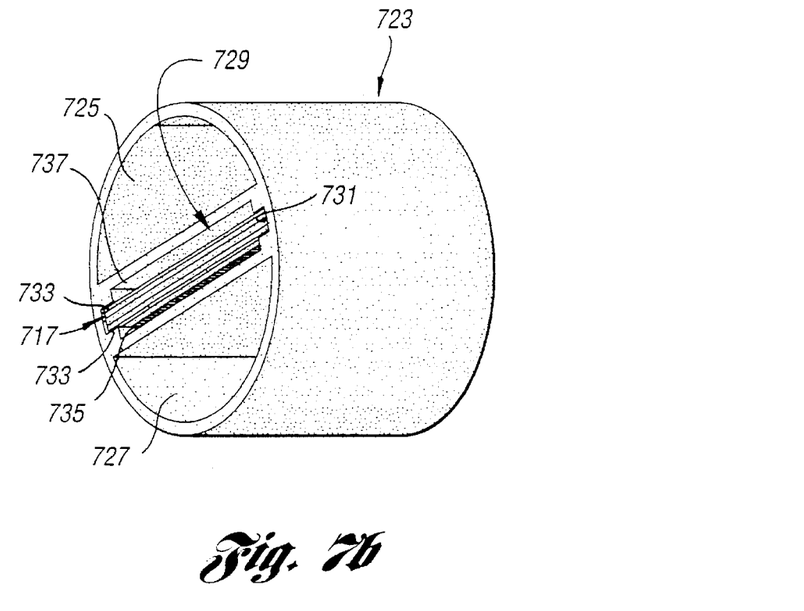

Filter element 717 divides the cylindrical housing (refer to FIG. 8) into two compartments, air passage 719 communicating with one compartment while water passage 707 communicates with the other passage. The corresponding cylindrical housing is illustrated in FIG. 7b. In FIG. 7b, compartments 725 and 727 of cylindrical housing 723 are not used. The filter element 717 is located in space 729 and sealed to housing 723 at 731 and 733. Surrounding filter element 717 are two recessed portions 735 and 737 which supply unfiltered air and water, being low volume passages.

Figure 8:
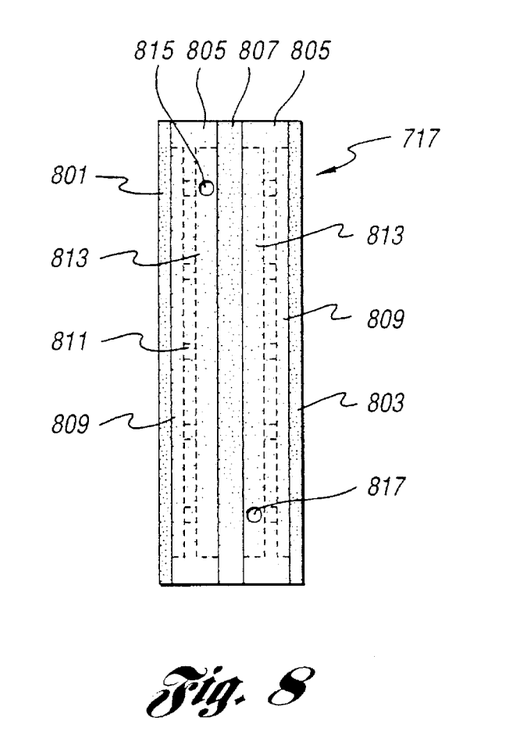

With reference to FIG. 8, filter element 717 is viewed from the outlet end. At 801 and 803 are the microporous air and water filtration membranes. Each of the filter grid elements 805 in this embodiment are similar, and are bonded to separator 807. Each filter grid contains numerous slots 809, the corresponding raised portions between the slots providing support for the filter membranes, the slots providing a path to through holes 811 which communicate with filtered air and water chambers 813. These chambers communicate with filtered air and water outlets 815 and 817 which, in turn, communicate with appropriately directed outlet passages which may be arranged in the outlet housing in a manner similar to that of the inlet housing of FIG. 7a or the outlet housing of FIG. 5.

The air filtration microporous membrane is preferably a hydrophobic membrane having a maximum pore size less than 1 μm. If complete freedom from microbial contamination is desired, the pore size should be less than 0.45 μm. Suitable filters are the VERSAPOR® microporous membranes available from Gelman Sciences, Inc. PTFE microporous membranes are also suitable. The air filtration membrane should be of adequate cross-sectional area to provide good air flow. Diameters of from 10 mm to about 40 mm, preferably 10–20 mm are suitable.

The water filtration microporous membrane is preferably a hydrophilic, self-wetting membrane. Suitable microporous membranes, having a maximum pore size less than 1 μm are available from Gelman Sciences as SUPOR® microporous membranes. As with the air filtration membrane, freedom from all microbial contamination can be achieved with pore sizes of 0.45 μm and smaller. The diameter of the water filtration membrane may be from 10 mm to 40 mm, preferably 10 mm to 15 mm. The outside diameter of the water filtration membrane is, in general, less than that of the air filtration membrane.

Because the microporous membranes are sealed to the filter structure, complete filtration of particulates, particularly microbes, down to the maximum pore size is possible. Due to their low cost, there is little incentive to reuse the filters, in contrast to the more expensive filters containing activated charcoal, which due to their cost must be used for a considerable time before replacement. Moreover, should a drop in pressure occur, no backflow of debris or microbes from the patient can flow back into the system. The result is a system of maximum hygienic efficiency as well as cost-effectiveness. The small size of the device, particularly the thickness, makes use of the device quite transparent to the dentist or hygienist.

Having now fully described the invention, it will be apparent to one of ordinary skill in the art that many changes and modifications can be made thereto without departing from the spirit or scope of the invention as set forth herein.

What is claimed is:

1. A combined air and water microfiltration device suitable for connection to a dental syringe, comprising:

a polymeric housing comprising an inlet housing, a support grid, and an outlet housing;

an air inlet passage, said air inlet passage in communication with an air chamber located within said polymeric housing between said inlet housing and said support grid, said air chamber containing a microporous air filtration membrane positioned such that all air passing through said device must pass through said microporous air filtration membrane;

said support grid located on the outlet side of said microporous air filtration membrane, said support grid supporting said microporous air filtration membrane, said support grid having through holes allowing filtered air to pass through said support grid to an air outlet passage in said outlet housing;

a water inlet tube passing through said inlet housing and said support grid into a water chamber formed between said support grid and a microporous water filtration membrane positioned such that all water passing through said device must pass through said microporous water filtration membrane;

said outlet housing supporting said microporous water filtration membrane against impinging water pressure, said outlet housing having a water outlet passage communicating with said microporous water filtration membrane.

2. The device of claim 1 wherein said microporous water filtration membrane and said microporous air filtration membrane are substantially plane parallel.

3. The device of claim 1 wherein one of said filtration membranes is washer-shaped and the other of said filtration membranes is disk-shaped, said filtration membranes plane parallel to each other and coaxially centered with respect to each other.

4. The device of claim 1 further comprising an extending cylindrical inlet sleeve adapted to be inserted into the outlet bore of a dental syringe handset, said cylindrical inlet sleeve having a circumferential groove adapted to receive an elastomeric O-ring located in said dental syringe handset bore.

5. The device of claim 4 wherein said cylindrical inlet sleeve contains a water inlet passage comprising a hollow tube within a polymeric sleeve extending axially away from said inlet housing, said polymeric sleeve containing a plurality of air passages formed by recesses between said hollow tube and said polymeric sleeve.

6. The device of claim 5 further comprising an outlet bore adapted to be connected to a syringe tip containing a central, hollow tubular water passage surrounded by an air passage.

7. The device of claim 5 further comprising an integral syringe tip containing a syringe water outlet passage and a syringe air outlet passage, said syringe water outlet passage communicating with said water outlet passage in said outlet housing, said syringe air outlet passage communicating with said air outlet passage in said outlet housing.

8. The device of claim 7 wherein said syringe water outlet passage comprises a central hollow tube surrounded by a polymeric sleeve containing a plurality of recesses between said central tube and said polymeric sleeve.

9. A combined air and water microfiltration device suitable for insertion into the outlet bore of a dental syringe handset, comprising:

an inlet housing of polymeric material having an inlet side and an outlet side, said inlet housing being substantially planar, and having a portion of reduced size in plane on the outlet side of the inlet housing forming a shoulder around the periphery of said inlet housing;

a cylindrical inlet sleeve adapted to be inserted into said outlet bore of said syringe handset, said cylindrical inlet sleeve containing a central tubular water inlet passage surrounded by one or more air inlet passages within said cylindrical inlet sleeve;

a support grid having an inlet side comprising a raised central portion having an opening through which said tubular water inlet passage passes, a mid-portion surrounding said central portion, said mid-portion having a plurality of radially extending slots extending from said central portion and terminating just within an outer portion of said support grid, said radially extending slots communicating with one or more through passages extending to an outlet side of said support grid, said outer portion of said support grid having one or more raised circumferential lands, at least one of said lands adapted to mate with said shoulder around the periphery of said inlet housing such that said support grid and said inlet housing are sealable between said at least one land and said shoulder;

an air chamber defined by a space between said inlet housing and said inlet side of said support grid, said air chamber in communication with said air inlet passage;

a microporous air filtration membrane located within said air chamber and proximate to the inlet face of said support grid, said microporous air filtration membrane positioned such that all air entering said air chamber from said air inlet passages must pass through said microporous air filtration membrane prior to passing through said through passages in said support grid;

an outlet housing having an inlet side and an outlet side, said outlet housing having a first circumferential step around the periphery defining a shoulder adapted to be sealed to a corresponding land on the outlet side of said support grid forming an outer seal, and a second circumferential step of reduced diameter adapted to be sealed to a corresponding face on the outlet side of said support grid forming an inner seal, the space between said outer seal and said inner seal defining an air passage in communication with said through passages in said support grid;

a water chamber defined by a space enclosed between said outlet side of said support grid and the portion of the inlet side of said outlet housing within said inner seal;

a microporous water filtration membrane located within said water chamber and proximate said inlet face of said outlet housing, said microporous water filtration membrane positioned such that all water passing through said water inlet passage to said water chamber must pass through said microporous water filtration membrane prior to exiting said device;

a water outlet passage in said outlet housing in communication with said microporous water filtration membrane;

wherein the air and water to be filtered by said device are maintained as separate fluid streams.

10. The device of claim 9 further comprising an integral syringe tip comprised of a polymeric syringe sleeve fixed to said outlet housing, a hollow tubular water outlet passage within said polymeric syringe sleeve, said tubular water outlet passage surrounded by one or more air outlet passages within said polymeric syringe sleeve.

11. The device of claim 9 wherein said outlet air passage and said outlet water passage are adapted to be connected to a separate syringe tip.

12. A combined air and water microfiltration device suitable for connection to a dental syringe, comprising:

an outlet housing having a water outlet passage and an air outlet passage and adapted to be sealed to a cylindrical filter retaining body, an inlet housing adapted to be sealed to said cylindrical filter retaining body;

a hollow, tubular water inlet passage extending through said inlet housing and communicating with a water chamber in said cylindrical filter retaining body;

one or more air inlet passages parallel to said water inlet passages, said air inlet passages communicating with an air chamber in said cylindrical filter retaining body;

a planar filter element comprising on one side an abutting water filtration microporous membrane in communication with a filtered water chamber on the side of the microporous water filtration membrane which abuts said one side of said filter element, said filtered water chamber in communication with said water outlet passage in said outlet housing; and an air filtration microporous membrane abutting a second side of said planar filter element in communication with a filtered air chamber on the side of the microporous air filtration membrane abutting said second side of said filter element, said filtered air chamber in communication with said air outlet passage in said outlet housing.

13. The device of claim 12 further comprising a polymeric sleeve containing said water inlet passage and said air inlet passage and adapted to mate with the outlet bore of a standard dental syringe handset.

\* \* \* \* \*